US009580473B2

(12) United States Patent
Weissman et al.

(10) Patent No.: US 9,580,473 B2
(45) Date of Patent: Feb. 28, 2017

(54) METHOD OF INHIBITING HIV-1 BINDING TO GENITAL EPITHELIA USING V3 LOOP-SPECIFIC PEPTIDES AND GP340-SPECIFIC ANTIBODIES

(75) Inventors: Drew Weissman, Wynnewood, PA (US); Earl Stoddard, Rockville, MD (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1615 days.

(21) Appl. No.: 12/303,985

(22) PCT Filed: Jun. 8, 2007

(86) PCT No.: PCT/US2007/013521
§ 371 (c)(1),
(2), (4) Date: Dec. 8, 2010

(87) PCT Pub. No.: WO2007/146132
PCT Pub. Date: Dec. 21, 2007

(65) Prior Publication Data
US 2011/0086028 A1      Apr. 14, 2011

Related U.S. Application Data

(60) Provisional application No. 60/812,095, filed on Jun. 9, 2006.

(51) Int. Cl.
| | | |
|---|---|---|
| *A61K 38/10* | (2006.01) | |
| *C07K 7/08* | (2006.01) | |
| *C07K 16/28* | (2006.01) | |
| *C07K 14/16* | (2006.01) | |
| *C07K 14/005* | (2006.01) | |
| *C07K 14/47* | (2006.01) | |
| *A61K 39/395* | (2006.01) | |
| *A61K 38/00* | (2006.01) | |

(52) U.S. Cl.
CPC ............ *C07K 14/005* (2013.01); *C07K 14/47* (2013.01); *C07K 16/28* (2013.01); *A61K 38/00* (2013.01); *A61K 38/10* (2013.01); *A61K 39/395* (2013.01); *C07K 7/08* (2013.01); *C07K 14/162* (2013.01); *C07K 2299/00* (2013.01); *C12N 2740/16111* (2013.01); *C12N 2740/16122* (2013.01)

(58) Field of Classification Search
CPC .................. A61K 39/395; A61K 38/10; C12N 2740/16111; C07K 7/08; C07K 14/162; C07K 16/28
See application file for complete search history.

(56) References Cited

U.S. PATENT DOCUMENTS 6,780,847 B2    8/2004    Boyd

OTHER PUBLICATIONS

Gali, Y., et al., 2010, In vitro evaluation of viability, integrity, and inflammation in genitcal epithelia upon exposure to pharmaceutical excipients and candidate microbicides, Antimicrob. Agents Chemother. 54(12): 5105-5114.*
Pope, M., and A. T. Haase, 2003, Transmission, actue HIV-1 infection and the quest for strategies to prevent infection, Nat. Med. 9(7):847-852.*
Holmskov, U., et al., Sep. 1999, Cloning of gp-340, a putative opsonin receptor for lung surfactant protein D, Proc. Natl. Acad. Sci. USA 96:10794-10799.*
Reina, J. J., et al., 2010, HIV microbicides: state-of-the-art and new perspectives on the development of entry inhibitors, Future Medicinal Chemistry 2(7):1141-1159.*
Wu, Z., et al., 2004, gp340 (SAG) binds to the V3 sequence of gp120 important for chemokine receptor interaction, AIDS Res. Human Retrovir. 20(6):600-607.*
Wu, Z., et al., 2006, The N-terminal SRCR-SID domain of gp-340 interacts with HIV type 1 gp120 sequences and inhibits viral infection, AIDS Res. Human Retrovir. 22(6):508-515.*
Sefton MV. Implantable Pumps. Critical Reviews in Biomedical Engineering. 14:201-240. (1987).
Buchwald et al. "Long-term, continuous intravenous heparin administration by an implantable infusion pump in ambulatory patients with recurrent venous thrombosis" Surgery. 88(4):507-16, Oct. 1980.
Saudek et al. "A Preliminary Trial of the Programmable Implantable Medication System for Insulin Delivery" N. Engl. J. Med. 321: 574, (1989).
Langer, R. "New methods of drug delivery" Science, 249, 1527-1533, (1990).
Cowsar and Dunn. "Biodegradable and Nonbiodegradable Fibrous Delivery Systems" Long-acting contraceptive delivery systems, pp. 145-163 (1984).
Ferguson T. H. et al. "Compudose: An Implant System for 5 Growth Promotion and Feed Efficiency in Cattle," J. Controlled Release 8, pp. 45-54 (1988).
Jackanicz. "In Long-acting contraceptive delivery systems" edited by Gerald I. Zatuchni 201-12. (1984).
Diczfalusy and Landgren. "Some Pharmacokinetic and Pharmacodynamic Properties of Vaginal Delivery Systems That Release Small Amounts of Progestogens at a Near Zero-Order Rate," pp. 213-227.
Roy S. and Mishell Jr. D. R. "Vaginal Ring Clinical Studies: Update," pp. 581-594, all in Zatuchni, G. L. et al. (eds.), Long-actingcontraceptive delivery systems (1984).
Scott and Smith GP. "Searching for peptide ligands with an epitope library" Science. ; 249(4967):386-390, Jul, 27, 1990.
Cwirla et al. "Peptides on phage: a vast library of peptides for identifying ligands" Proc Natl Acad Sci USA. ; 87:6378-6382. (1990).
Devlin et al. "Random Peptide Libraries: A Source of Specific Protein Binding Molecules" Science 249:404-406 Jul. 27, 1990.

(Continued)

*Primary Examiner* — Jeffrey Parkin
(74) *Attorney, Agent, or Firm* — Mark S. Cohen; Pearl Cohen Zedek Latzer Baratz LLP

(57) ABSTRACT

This invention relates to methods compositions and devices for inhibiting infection of a subject's host cell by HIV. Specifically, the invention relates to methods and compositions capable of inhibiting the binding and subsequent infection by HIV of a host cell through the inhibition of the interaction between gp-340 expressed on the cell surface and V3 loop on the HIV envelope and devices comprising these compositions.

10 Claims, 7 Drawing Sheets

(56) References Cited

OTHER PUBLICATIONS

Lam et al. "Rational Design of Potent, Bioavailable, Nonpeptide Cyclic Ureas as HIV Protease Inhibitors" Science 263: 380-384 (1994).
Erickson. "Design and Structure of Symmetry-Based Inhibitors of HIV-1 Protease" Perspect. Drug Dis. Design 1: 109-128 (1993).
Wlodawer A and Erickson JW. "Structure-based inhibitors of HIV-1 protease" Annu Rev Biochem.; 62:543-585, (1993).
Appelt k "Crystal structures of HIV-1 protease-inhibitor complexes", Pers in Drug Disc & Design,, 1:23-48, (1993).
Kraulis. "A Program to Produce Both Detailed and Schematic Plots of Protein Structures" J Appl. Crystallogr. 24, 946-950 (1991).
Fichorova et al. "Generation of papillomavirus-immortalized cell lines from normal human ectocervical, endocervical, and vaginal epithelium that maintain expression of tissue-specific differentiation proteins" Biol Reprod. ; 57:847-855, (1997).
Wu et al. "gp340 (SAG) Binds to the V3 Sequence of gp120 Important for Chemokine Receptor interaction" AIDS Res. Hum, Retroviruses. vol. 20, No. 6, pp. 600-607, Jun. 1, 2004.
Holmskov et al. "Cloning of gp-340, a putative opsonin receptor for lung surfactant protein D" Proc. Natl. Acad. Sci. USA vol. 96, pp. 10794-10799, Sep. 30, 1999.
Mollenhauer et al. "DMBT1 Encodes a Protein Involved in the Immune Defense and in EpitheliaΛ Differentiation and is Highly Unstable in Cancer" Cancer Res. vol. 60, pp. 1704-1710, Mar. 15, 2000.
Wu et al. "The N-Terminal SRCR-SID Domain of gp-340 Interacts with HIV Type 1 gp120 Sequences and Inhibits Viral Infection" AIDS Res, Hum. Retroviruses. vol. 22, No. 6, pp. 508-515, Jun. 1, 2006.
Kang t al. "DMBT1, a regulator of mucosal homeostasis through the linking of mucosal defense and regeneration" FEBS Lett. vol. 540, pp. 21-25, Mar. 12, 2003.
International Search Report Appliaction No. PCT/US 07/13521 Date of Mailing Jan. 27, 2009.
Abuchowski et al. "Immunosuppressive properties and circulating life of Achromobacter glutaminase-asparaginase covalently attached to polyethylene glycol in man" Cancer Treat Rep. 65(11-12): 1077-81 1981.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Goodson, in Medical Applications of Controlled Release, supra, vol. 2, pp. 115-138 (1984).

* cited by examiner

SEQUENCE LISTING

<160> NUMBER OF SEQ ID NOS: 4

<210> SEQ ID NO 1
<211> LENGTH: 15
<212> TYPE: PRT
<213> ORGANISM: Human

<400> SEQUENCE: 1

Val Gln Ile Asn Cys Thr Arg Pro Asn Tyr Asn Lys Arg Lys Arg
1               5                   10                  15

<210> SEQ ID NO 2
<211> LENGTH: 15
<212> TYPE: PRT
<213> ORGANISM: Human

<400> SEQUENCE: 2

Cys Thr Arg Pro Asn Tyr Asn Lys Arg Lys Arg Ile His Ile Gly
1               5                   10                  15

<210> SEQ ID NO 3
<211> LENGTH: 15
<212> TYPE: PRT
<213> ORGANISM: Human

<400> SEQUENCE: 3

Lys Glu Ala Thr Thr Thr Leu Phe Cys Ala Ser Asp Ala Lys Ala
1               5                   10                  15

<210> SEQ ID NO 4
<211> LENGTH: 15
<212> TYPE: PRT
<213> ORGANISM: Human

<400> SEQUENCE: 4

Arg Cys Ile His Asn Arg Thr Ile Lys Gly Pro Tyr Asn Lys Arg
1               5                   10                  15

METHOD OF INHIBITING HIV-1 BINDING TO GENITAL EPITHELIA USING V3 LOOP-SPECIFIC PEPTIDES AND GP340-SPECIFIC ANTIBODIES

CROSS-REFERENCE TO RELATED APPLICATIONS

This application is a National Phase Application of PCT International Application No. PCT/US07/13521, International Filing Date Jun. 8, 2007, claiming priority of United States Provisional Patent Application, 60/812,095, filed Jun. 9,2006, both which are incorporated herein by reference in their entirety.

FIELD OF INVENTION

This invention is directed to methods, compositions and devices for inhibiting infection of a host cell by HIV. Specifically, the invention relates to methods and compositions capable of inhibiting the binding and subsequent infection by HIV of host cells through the inhibition of the interaction between gp-340 expressed on the cell surface and V3 loop on the HIV envelope.

BACKGROUND OF THE INVENTION

HIV continues to spread with nearly 40 million infected individuals and over 5 million newly infected every year. The principle means of infection remains heterosexual transmission. In many areas of the world, particularly Sub-Saharan Africa, HIV infection has become more prevalent in women than men (www.unaids.org). This trend in conjunction with discriminatory sexual rights for women in many parts of Asia and Africa makes it important to identify the mechanisms of male-to-female spread of HIV and to implement new methods for preventing sexual transmission. Normally, the mucosal barrier acts as a significant blockade for pathogens seeking to gain entry into the human body. HIV enters either through breaks in this barrier or through some active mechanism that allows it to transverse the mucosal barrier. Identification of mediators of transmission is therefore very desirable.

Macaque studies indicate that the first targets of SIV infection during non-traumatic vaginal application are Langerhans cells (LCs), sub-epithelial dendritic cells (DCs) and CD4[+] T cells of the lower genital tract. The lower genital tract barrier is composed of a columnar monolayer in the endocervix and stratified squamous epithelium in the vagina and ectocervix along with their associated mucous and glycoprotein secretions. The necessary events in transmission preceding infection of LCs, sub-epithelial DCs and CD4[+] T cells remain unclear. In vitro models of female genital tissue have been designed to explore transmission, but their in vivo relevance is controversial.

Disruption of these epithelial barriers by ulcerating lesions or other local factors allowing direct access to underlying cells capable of propagating virus is a proposed mechanism for penetrating the outer mucosa. However, infection in the presence of a seemingly undamaged epithelium also occurs. Previous experiments have suggested that primary vaginal epithelial cells can sequester and transmit HIV to activated PBMCs in culture, even though the epithelial cells do not express significant levels of virus receptors[6]. This indicates that other factors within this subset of cells may interact directly with HIV and facilitate virus transfer to target cells

SUMMARY OF THE INVENTION

In one embodiment, the invention provides a method of inhibiting binding of an immunodeficiency virus to a genital tract epithelial cell in a subject, comprising the step of: contacting the genital tract epithelial cell with an effective amount of an agent capable of inhibiting the binding between immunodeficiency virus and gp-340, thereby inhibiting binding of the virus onto the genital to tract epithelial cell.

In another embodiment, the invention provides a composition for treating immunodeficiency virus binding and subsequent infection of a target cell comprising: an effective amount of an agent capable of binding to gp-340, an effective amount of an antibody specific against gp-340 that is expressed on the host cell surface or a fragment thereof, or their combination.

In one embodiment, the invention provides a method of inhibiting attachment of an immunodeficiency virus to a host cell, comprising the step of contacting the host cell with a gp340-specific antibody or a fragment thereof, thereby eliminating the attachment site on the host cell for the virus.

In another embodiment, the invention provides a method of inhibiting attachment of an immunodeficiency virus to a host cell, comprising the step of contacting gp340 expressed on a host cell, thereby eliminating the attachment site for the virus' envelope.

In one embodiment, the invention provides a contraceptive device comprising: an agent capable of binding to gp340 expressed on a host cell; an effective amount of an antibody or a fragment thereof specific against gp-340 that is expressed on the surface of a vaginal, an endocervical or an ectocervical primary epithelial cell, or a combination thereof.

In another embodiment, the invention provides a method to identify a ligand to membrane bound gp340, comprising: contacting a membrane bound gp340 with a candidate ligand, under conditions wherein, in the absence of said candidate ligand, said membrane bound gp340 is capable of attaching to the third hypervariable region of gp-120 (V3 loop) expressed on an immunodifeciency virus' envelope; and detecting concentration or activity of bound virus' envelope, wherein reduction in concentration or activity of said bound virus' envelope in the manner associated with the binding of said membrane bound gp340 indicates that said candidate ligand is a membrane bound gp340 ligand.

In another embodiment, the invention provides a method of using a three-dimensional structure of membrane bound gp340 in an agent screening assay comprising the steps of: selecting of a potential agent by performing rational drug design based on said three-dimensional structure, wherein said selecting is performed in conjunction with computer modeling; contacting the potential agent with a first polypeptide comprising an amino acid sequence having at least 75% homology to a first predetermined region of the membrane bound gp340; and detecting the binding affinity of the potential agent with said first polypeptide, whereby a potential agent is selected as an agent if the potential agent binds to said first polypeptide.

DETAILED DESCRIPTION OF THE INVENTION

Figure 1:
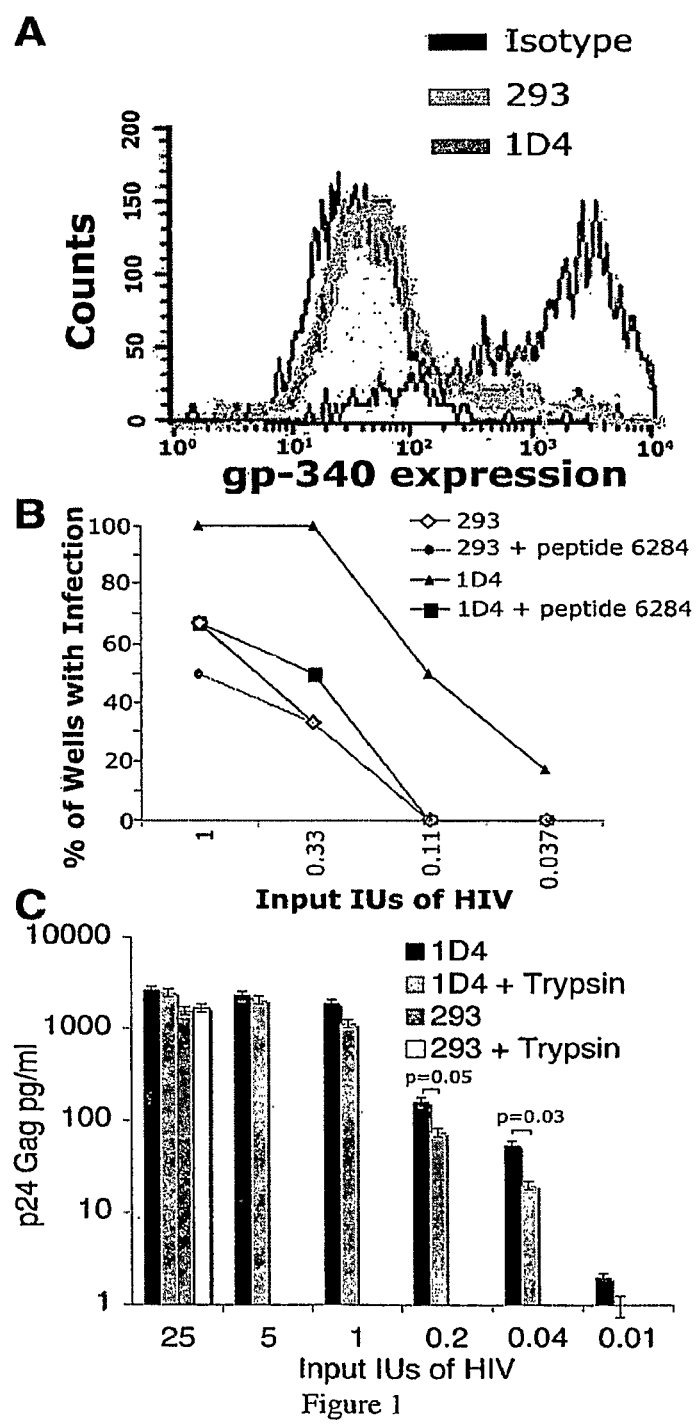
FIG. 1. 293 cells stably expressing cell surface gp-340 enhance the transfer of HIV to target cells. (A) 293 cells and a clone, 1D4, stably expressing gp-340, were stained for surface expression of gp-340 using rabbit polyclonal antibody 1527. Isotype control stained cells shown are 293 cells, but the 1D4 clone gave the same pattern. (B) Clone 1D4 and 293 cells were pulsed with increasing IU of HIV BL2 virus with or without a V3-derived peptide 6284 (10 μg/ml) that blocks Env-gp-340 binding, washed and exposed to PHA-blasts for 7 days. IUs were calculated using PHA-blasts as target cells in a $TCID_{50}$ assay. Experiment was performed in replicates of 6 wells per viral addition and data is expressed as the percentage of the wells that became infected.

This invention relates in one embodiment to methods and compositions capable of inhibiting the fusion or binding and infection by HIV of a host cell through the inhibition of the interaction between gp-340 expressed on the cell surface and V3 loop on the HIV envelope.

In one embodiment, during sexual transmission of HIV in females, the first cells infected are submucosal $CD4^+$ T cells and dendritic cells of the lower genital tract. HIV is segregated from these target cells by an epithelial cell layer that can be bypassed even when healthy and intact. Applicants have identified a novel host protein, gp-340, that is expressed on genital epithelium and binds HIV envelope via a specific protein-protein interaction. This binding increases both the infectious titer and preserves infectivity of the virus. The findings demonstrate in one embodiment the mechanism of viral entry during heterosexual transmission where HIV binds intact genital epithelia, which then promotes the initial events of infection. This finding allows for the development of compositions and methods for blocking HIV transmission.

Therefore, according to this aspect of the invention and in one embodiment, the invention provides a method of inhibiting binding of an immunodeficiency virus to a genital tract epithelial cell in a subject, comprising the step of: contacting the genital tract epithelial cell with an effective amount of an agent capable of inhibiting the binding between immunodeficiency virus and gp-340, thereby inhibiting binding of the virus onto the genital tract epithelial cell.

In one embodiment, the methods provided herein for inhibiting binding of an immunodeficiency virus to a genital tract epithelial cell in a subject, are used for inhibiting HIV-1 infection.

A number of host factors have been shown to interact with HIV and influence the infection. In one embodiment, intercellular adhesion molecule—grabbing integrin, specific for dendritic cells (DC-SIGN), which is expressed mainly on macrophages and DCs, binds and sequesters HIV and subsequently presents the virus to target CD4+ T cells for infection. The syndecan family of receptors has been shown to bind HIV-1 through glycosylation-based interactions between its heparin sulfate moieties and HIV-1 gp120 and to mediate trans-infection of HIV. In another embodiment, Mannose receptors (MRs) on primary monocyte-derived macrophages (MDMs) can bind to HIV and facilitate transmission to T cells in coculture, as well. Each of these molecules recognizes components of the glycan shield of HIV-1 Env and uses this binding to mediate enhanced transmission. Salivary agglutinin (SAG) is another host protein that binds HIV-1 Env, but in a different manner. SAG, first identified as a component of human saliva with anti-HIV-1 activity, was subsequently shown to form a protein-protein interaction with the HIV-1 gp120 protein. These studies demostrate that a specific V3 loop peptide is sufficient to bind gp-340. SAG is a splice variant encoded by the DMBT1 gene, which also encodes other variants including cell surface-associated gp-340 that acts as an immune scavenger receptor and epithelial cell differentiation antigen. Gp-340 plays a role in innate immune surveillance of bacteria in the lung and oral cavities and in the host defense against influenza A virus. Also, a correlation has been drawn between mutations in the DMBT1 gene and occurrence of certain epithelial-derived malignant tumors. As described herein, gp-340 expressed on primary female genital epithelial cells binds HIV-1 and enhances transmission by increasing infectivity and half-life of the virus. Therefore, inhibiting the ability of gp-340 to bind HIV-1 will prevent or suppress or inhibit, in one embodiment, the transmission of HIV by decreasing infectivity and shortening the half-life of the virus.

According to one embodiment of the invention, provided herein is a method of inhibiting binding of an immunodeficiency virus to a genital tract epithelial cell in a subject, comprising the step of: contacting the genital tract epithelial cell with an effective amount of an agent capable of inhibiting the binding between immunodeficiency virus and gp-340, thereby occupying the binding site for the virus and preventing binding of the virus onto the genital tract epithelial cell and subsequent infection of target cells, wherein the agent is capable of inhibiting the binding to the third hypervariable region of gp-120 (V3 loop) expressed on the virus' envelope by gp-340; an effective amount of an antibody or a fragment thereof specific against membrane bound gp-340 on said genital tract epithelial cell, or a to combination thereof.

Heterosexual transmission of HIV-1 is an inefficient process with population studies suggesting that the risk of infection per exposure is 0.01 to 0.15%. In one embodiment, the presence of ulcerative and non-ulcerative sexually transmitted diseases (STDs) increases this risk per exposure. In one embodiment, mucosal penetrating lesions with surrounding inflammation and target cells in ulcerative STDs are a mechanism for increased transmission, while in another embodiment the presence of increased targets of infection in epithelial and subepithelial tissues may enhance infection in non-ulcerative STDs. In one embodiment, passive diffusion through tiny perforations in the epithelial layer may facilitate the infection by HIV. The results described herein, as well as the observation that genital tract epithelial cells express an HIV Env-binding protein that increase both viral infectivity and infectious half-life suggest a potential novel mechanism for mucosal transmission.

A number of different HIV-binding macromolecules have been identified. In the context of vaginal and cervical epithelia, heparin sulfate molecules on the cell surface have been shown to facilitate some binding of HIV-1. However, this glycosylation-based interaction was not the only means by which HIV-1 bound to these cells as evidenced by the inability to completely abate binding in the presence of specific inhibitors. Other HIV-1 binding molecules such as CCR5, CXCR4, CD4, MR, and DC-SIGN are not expressed on genital epithelia, although their potential importance to infection in many compartments of the body are known in the art. Thus, genital tract epithelial cells can mediate trans-infection of HIV-1 through specific protein-protein interactions between cell-associated gp-340 and HIV-1 Env. In one embodiment, cell surface- and endosome-associated gp-340 are present in alveolar macrophages, suggesting that gp-340 is capable of trafficking to intracellular compartments.

In one embodiment, the immunodeficiency virus whose infectivity is sought to be prevented using the methods and compositions described herein is human immunodeficiency virus (HIV), simian immunodeficiency virus (SIV), or a combination thereof.

HIV referes in one embodiment to a retrovirus that causes immunosuppression in humans (HIV disease), and leads to a disease complex known as the acquired immunodeficiency syndrome (AIDS). HIV disease is characterized by progressive functional deterioration of the immune system. In one embodiment, the immunodeficiency virus whose infectivity is sought to be prevented using the methods and compositions described herein is human immunodeficiency virus (HIV).

The simian immunodeficiency viruses (SIVs) refer in one embodiment to non-human, primate lentiviruses related to the human immunodeficiency viruses (HIV-1 and HIV-2), the causative agents of AIDS in humans. SIV has been isolated from several species of primates, including in one embodiment, rhesus monkeys ($SIV_{mac}$), or African green monkeys ($SIV_{agm}$), sooty mangabey monkeys ($SIV_{sm}$), and mandrills ($SIV_{mnd}$) in other embodiments. The extensive similarity of SIV to HIV in genetic organization and biological properties indicates that SIV systems are ideally suited for study of AIDS pathogenesis and vaccine strategies. Thus, SIV genetic relationships also provide clues to the evolution, origin, and possible interspecies transmission of lentiviruses in primates. In one embodiment, the immunodeficiency virus whose infectivity is sought to be prevented using the methods and compositions described herein is simian immunodeficiency virus (SIV).

In one embodiment, the agent capable of attaching to gp-340 and blocking the binding of the third hypervariable region of gp-120 (V3 loop), which is used in the methods, compositions and contraceptives described herein, is a V3 loop-specific peptide. The protein-protein interaction between gp-340 and HIV-1 Env is uncommon amongst identified host HIV-1 Env-binding molecules. Most identified non-CD4 or coreceptor interactions with Env, including DC-SIGN, MR and syndecans are mediated through glycosyl groups that coat viral proteins. The Env protein of HIV-1 is covered with 24 N-glycosylation moieties whose sugars serve to shield it from immune recognition. Binding via glycosyl moieties is relatively non-specific, thus directed inhibitors of the interaction have reduced potential. In one embodiment, the binding site for gp-340 is near the base of the V3 loop of Env. The SRCR domain of gp-340 mediates this binding to envelope. Prior studies with SAG demonstrated that the addition of soluble CD4 enhanced binding to Env suggesting binding is to a site that is partially shielded supporting the V3 loop as the binding site of gp-340 to Env.

In one embodiment, it is the combined binding of both the V3 loop and the bridging sheet domains of Env that mediate coreceptor binding leading to fusion and infection. In another embodiment, Envs lacking V3 loops infect cells as well, suggesting its presence is not absolutely required for infection. The results described in the examples herein demonstrate that gp-340 binding to Env does not interfere with viral fusion and the presence of gp-340 on a cell with CD4 and coreceptor, in fact, promotes fusion.

In one embodiment, the V3 loop-specific peptide, used as the agent capable of blocking binding of the third hypervariable region of gp-120 (V3 loop) to gp-340, which is used in the methods, compositions and contraceptives described herein, comprises the following amino acid sequence: VQINCTRPNYNKRKR (SEQ ID NO. 1), CTRPNYNKRKRIHIG (SEQ ID NO. 2) or their combination. In another embodiment, the V3 loop-specific peptide comprises the amino acid sequence set forth in SEQ ID NO. 2.

In one embodiment, immunohistochemical staining of surgically excised tissue with gp-340 specific monoclonal antibodies demonstrated expression on both vaginal and cervical epithelial cells. For vaginal sections, the expression was seen diffusely on the stratified squamous layer. This would be a relevant expression site for HIV-1 infection since the genital mucosa and epithelial cell layer act as the principle barrier separating HIV-1 from its target dendritic and T cells. Surprisingly, cervical staining for gp-340 is strongest in one embodiment along the basal membrane of the columnar epithelial cells but is also present along the apical region of these cells. The polar expression is noteworthy because of described functions of another mammalian homologue of gp-340. In one embodiment cells derived from these tracts express gp-340 and that this expression of gp-340 results in their ability to trans-infect. In one embodiment, the agent capable inhibiting the attachment to the third hypervariable region of gp-120 (V3 loop) to gp-340, which is used in the methods, compositions and contraceptives described herein, is a monoclonal antibody, specific for the membrane-bound gp-340.

In another embodiment, the term "peptide", when in reference to any peptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C.A. Ramsden Gd., Chapter 17.2, F. Choplin Pergamon Press (1992). It is to be understood that any amino acid sequence whether obtained naturally or synthetically, by any means, exhibiting sequence, structural, or functional homology to the peptides described herein are considered as part of this invention As used herein, the terms "homology", "homologue" or "homologous", in any instance, indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino is acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% correspondence with the indicated sequence. In another embodiment, the amino acid sequence or nucleic acid sequence exhibits at least 99% correspondence with the indicated sequence. In another embodiment, the amino acid sequence or nucleic acid sequence exhibits 95-100% correspondence with the indicated sequence. Similarly, as used herein, the reference to a correspondence to a particular sequence includes both direct correspondence, as well as homology to that sequence as herein defined.

Homology, as used herein, may refer to sequence identity, or may refer to structural identity, or functional identity. By using the term "homology" and other like forms, it is to be understood that any molecule, whether nucleic acid or peptide, that functions similarly, and/or contains sequence identity, and/or is conserved structurally so that it approximates the reference sequence, is to be considered as part of this invention.

Protein and/or peptide homology for any peptide sequence listed herein may be determined by immunoblot analysis, or via computer algorithm analysis of amino acid sequences, utilizing any of a number of software packages available, via methods well known to one skilled in the art. Some of these packages may include the FASTA, BLAST, MPsrch or Scanps packages, and may employ the use of the Smith and Waterman algorithms, and/or global/local or BLOCKS alignments for analysis, for example.

In one embodiment, the term "antibody" include complete antibodies (e.g., bivalent IgG, pentavalent IgM) or fragments of antibodies in other embodiments, which contain an antigen binding site. Such fragment include in one embodiment Fab, F(ab')$_2$, Fv and single chain Fv (scFv) fragments. In to one embodiment, such fragments may or may not include antibody constant domains. In another embodiment, F(ab)'s lack constant domains which are required for complement fixation. scFvs are composed of an antibody variable light chain ($V_L$) linked to a variable heavy chain ($V_H$) by a flexible linker. scFvs are able to bind antigen and can be rapidly produced in bacteria. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

The antibodies described herein can be monoclonal antibodies (Mab) in one embodiment, or polyclonal antibodies in another embodiment. Antibodies of the invention which are useful for the compositions, methods and contraceptives described herein can be from any source, and in addition may be chimeric. In one embodiment, sources of antibodies can be from a mouse, or a rat, or a human in other embodiments. Antibodies of the invention which are useful for the compositions, methods and contraceptives of the invention have reduced antigenicity in humans, and in another embodiment, are not antigenic in humans. Chimeric antibodies as described herein contain in one embodiment, human amino acid sequences and include humanized antibodies which are non-human antibodies substituted with sequences of human origin to reduce or eliminate immunogenicity, but which retain the binding characteristics of the non-human antibody. In another embodiment, the agent capable of attaching to gp-340 and blocking the binding of the third hypervariable region of gp-120 (V3 loop), which is used in the methods, compositions and contraceptives described herein, is the gp-340-specific antibody mAb116, represented by the amino acid sequence (SEQ ID NO. X) mAb303, pAb1527, DAPA or their combination.

In one embodiment, the antibody, a fragment thereof, or their combination, exhibit substantially complimentarity to their target sequence, which may be a protein, such as gp340 protein, or V3 loop-specific peptide in other embodiments. In another embodiment, "complementary" indicates that the oligopeptide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present on a target protein sequence (excluding RNA and DNA equivalents). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the host cell for which the binding by HIV or SIV is sought to be inhibited using the methods, compositions and contraceptives described herein, is a vaginal cell, or an endocervical or an ectocervical primary epithelial cell or their combination in other embodiments.

In one embodiment, the method of inhibiting infection by an immunodeficiency virus of a host cell in a subject, comprising the step of: administering to the subject an effective amount of an agent used in the compositions and contraceptives described herein, is capable of attaching to gp-340 and blocking the binding to the third hypervariable region of gp-120 (V3 loop) expressed on the virus' envelope; an effective amount of an antibody or a fragment thereof specific against gp-340 that is expressed on the host cell surface, or a combination thereof, thereby eliminating the attachment site for the virus and preventing binding of the virus onto the host cell and subsequent infection of a target cell, further comprises the step of administering to the subject an effective amount of a soluble gp-340.

In one embodiment, Gp-340 secreted from salivary glands is known as SAG. Oral mucosal cells do not express cell surface gp-340, but the oral cavity has high levels (492±40 ng/ml) of soluble gp-340. In one embodiment, secreted SAG inhibits HIV infection by binding to Env. This difference in promotion versus inhibition of infection by cell associated versus soluble gp-340 is a property that is similarly observed for CD4, another HIV Env binding molecule with protein-protein interaction. In one embodiment, genital tract secretions have very low levels of soluble gp-340 (0.1-0.5 µg/ml). The disparity between high levels of soluble gp-340 and inhibition of HIV infection in the oral cavity in contrast to the genital tract where there are high levels of cell associated enhancing gp-340 and little HIV inhibiting soluble gp-340 account in another embodiment for the differences in transmission between these two locations.

In another embodiment, the method of inhibiting infection by an immunodeficiency virus of a host cell in a subject, comprising the step of: administering to the subject an effective amount of an agent used in the compositions and contraceptives described herein, is capable of attaching to gp-340 and blocking the binding to the third hypervariable region of gp-120 (V3 loop) expressed on the virus' envelope; an effective amount of an antibody or a fragment thereof specific against gp-340 that is expressed on the host cell surface, or a combination thereof, thereby eliminating the attachment site for the virus and preventing binding of the virus onto the host cell and subsequent infection, further comprises the step of administering to the subject an effective amount of 2,5-dimethoxy-substituted 5-bromopyridyl thiourea (PHI-236), nonoxynol-9 or a combination thereof, all which are known in other embodiments to destroy HIV or SIV.

In one embodiment 2,5-dimethoxy-substituted 5-bromopyridyl thiourea (PHI-236) refers to non-nucleoside reverse transcriptase inhibitors (NNRTIs), which bind to an allosteric site on RT. In other embodiments, other NNRTIs may be used in the methods, compositions and contraceptives described herein. These include, but are not limited to rationally designed NNRTIs deduced from changes in binding pocket size, shape and residue character that result from clinically observed NNRTI resistance-associated mutations and exhibit high binding affinity for HIV-1 RT and robust anti-HIV activity against the wild-type and drug-escape mutants without cytotoxicity. In one embodiment, membrane permeable tight binding NNRTIs have the ability to inactivate cell-free as well as cell-associated HIV-1 in semen without metabolic activation and are used in the methods, compositions and contraceptives described herein. In other embodiments, the NNRTIs include thiourea-PETT (where PETT refers to phenethylthiazolylthiourea) derivatives (PHI-236, PHI-346 and PHI-443), urea-PETT derivatives (MN-150), oxypyrimidines (S-DABOs), thiocarboxanilides (UC-781) and diarylpyrimidines (TMC-120). In another embodiment, virucidal properties such as those exhibited by spermicides such as nonoxynol-9 and octoxynol; benzalkonium chloride; menfegol; and chlorhexidine in other embodiments, are used in the methods, compositions and contraceptives described herein.

In one embodiment, the compositions described herein, are used to carry out the methods described herein. In one embodiment, provided herein is a composition for treating immunodeficiency virus binding and infection comprising:

an effective amount of an agent capable of binding to gp-340, an effective amount of an antibody specific against gp-340 that is expressed on the host cell surface or a fragment thereof, or their combination. In another embodiment, any composition described hereinabove as part of the methods embodiments, is used in the compositions described herein. In one embodiment, the invention provides a composition for preventing immunodeficiency virus binding and infection comprising: an effective amount of an agent capable of attaching to gp-340, an effective amount of an antibody or a fragment thereof specific against gp-340 that is expressed on the host cell surface, a non-nucleoside reverse transcriptase inhibitor (NNRTI), a spermicide or any combination thereof. In another embodiment, the composition, which may be used in the methods and contraceptives described herein further comprise a pharmaceutically acceptable carrier, excipient, flow agent, processing aid, diluent or a combination thereof.

In one embodiment, the composition described herein, which may be used in the methods and contraceptives described herein, is in a form suitable for oral, intravenous, intraaorterial, intramuscular, intravaginal, subcutaneous, parenteral, transmucosal, transdermal, or topical administration. In one embodiment, the topical form of the composition described herein is in the form of a cream, an ointment, a suspension, an emulsion, a gel or a combination thereof.

In one embodiment, the carrier, excipient, lubricant, flow aid, processing aid or diluent, used ion the compositions described herein, is a gum, a starch, a sugar, a cellulosic material, an acrylate, calcium carbonate, magnesium oxide, talc, lactose monohydrate, magnesium stearate, colloidal silicone dioxide or mixtures thereof.

The formulation may in one embodiment, be in the form of a vaginal suppository, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, anticoagulant, preservative, surface-active or dispersing agent or a combination thereof. In one embodiment gp-340 is expressed on rectal mucosa and a rectal suppository with an inhibitor may be used to block rectal transmission of HIV.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

In one embodiment, the composition is a particulate composition coated with a polymer (e.g., poloxamers or poloxamines). Other embodiments of the compositions of the invention incorporate particulate forms protective coatings, protease inhibitors or permeation enhancers for various routes of administration.

The compounds utilized in the methods and compositions of the present invention may be present in the form of free bases in one embodiment or pharmaceutically acceptable acid addition salts thereof in another embodiment. In one embodiment, the term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I are prepared in another embodiment, from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, in another embodiment, the appropriate acid or base with the compound.

In one embodiment, the term "pharmaceutically acceptable carriers" includes, but is not limited to, may refer to 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

In one embodiment, the compositions described herein, may include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Examples of suitable oily vehicles or solvents are vegetable or animal oils such as sunflower oil or fish-liver oil. Preparations can be effected both as dry and as wet granules. For topical administration, the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil.

In general, water, saline, aqueous dextrose and related sugar solutions, and glycols such as propylene glycols or polyethylene glycol are preferred liquid carriers, particularly for injectable solutions.

In addition, the composition can contain minor amounts of auxiliary substances such as wetting or emulsifying agents, pH buffering agents which enhance the effectiveness of the active ingredient.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptor.

In one embodiment, the composition described herein, or the preparation used in the methods described herein, can be delivered in a controlled release system. For example, the plasma isolated from a vitiligo patient, or in another embodiment, from a melanoma patient in which antibodies to melanoma antigens are identified, may be administered using intravenous infusion, an implantable osmotic pump, a transdermal patch, liposomes, colloidosomes, polymerosomes or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In another embodiment, a controlled release system can be placed in proximity to the therapeutic target, i.e., the melanoma site, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Such compositions are in one embodiment liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycoic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors, or permeation enhancers for various routes of administration, including vaginal.

In another embodiment, the compositions of this invention comprise one or more, pharmaceutically acceptable carrier materials. In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired.

The events triggering the release of an agent capable of attaching to gp-340, an effective amount of an antibody or a fragment thereof specific against gp-340 that is expressed on the host cell surface, or a combination thereof, may be the same in one embodiment, or different in another embodiment. Events triggering the release of the active components may be exposure to moisture in one embodiment, lower or higher pH in another embodiment, or temperature threshold in another embodiment. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

For intravaginal administration, the agents described herein may be formulated as is known in the art for direct application to the vaginal area. Forms chiefly conditioned for vaginal application are creams, or milks, gels, dispersions, micro-emulsions, lotions thickened to a greater or lesser extent, impregnated pads, ointments, aerosol formulations (e.g., sprays or foams), creams, lotions, pastes, jellies, sprays, and aerosols in other embodiments. In one embodiment, the composition can be formulated to be part of an adhesive polymer, such as polyacrylate or acrylate/vinyl acetate copolymer.

In another embodiment, ointments and creams may be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. The percent by weight of an agent of the invention present in a formulation will depend on various factors, but generally will be from about 0.01% to about 98% of the total weight of the formulation, and typically about 0.1 to about 90% by weight.

In some embodiments, the active ingredients can be formulated with oleaginous bases or ointments to form a semisolid composition with a desired shape. For example, the composition can be shaped for easy insertion into an orifice such as the vagina. This class of formulations comprises the active ingredients and hydrocarbon-based semisolids containing dissolved and/or suspended bacteriostats/preservatives/spermicides and a buffer system. The petrolatum component in these bases can be any paraffin ranging in viscosity from mineral oil employing incorporated isobutylene, colloidal silica, or stearate salts to paraffin waxes. White and yellow petrolatums are used in one embodiment of such petrolatum components. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to 10.sup.6 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

Oil-In-Water emulsion bases can also be utilized in the compositions, inserts and articles of the invention. These systems are semisolid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

Inserts and suppositories containing the active ingredients can be, for example, oleaginous in nature that melt at body temperature, or polyethylene glycol-based compositions that dissolve in mucosal (e.g. vaginal) fluids. Additional bases for suppositories are glycerin and glycerinated gelatin.

The active ingredients can be formulated into inserts, articles, tampons, transdermal patches, bandages, and dressings using buffered gels made with gelling agents. Some examples of these gelling agents are: cellulosics, cationic polymers, polyoxyalkylenes, and carboxyvinyl polymers. Cellulosics useful in the formulations of the invention include, for example, methyl cellulose, carboxymethyl cellulose, hydroxyethyl cellulose, and hydroxypropyl cellulose. Cationic Polymers useful in the formulations of the invention include "Polyquaternium-10", a polymeric quaternary ammonium salt of hydroxyethyl cellulose reacted with a trimethyl ammonium-substituted epoxide, and the like. Polyoxyalkylenes useful in the invention include polyoxyethylene-polyoxypropylene esters of lanolin and derivatives thereof. Carboxyvinyl polymers useful for the formulations of the invention include cross-linked acrylic acid polymers, e.g., those commercially available from B. F. Goodrich Co., Akron, Ohio, under the designation CARBOPOL™.

The compositions described herein may, in one embodiment be in the form of a gel, cream, tablet, capsule, suppository, film, or any other pharmaceutically acceptable form that is tolerated by epithelial cells (e.g. the mucosa) and does not wash away easily.

In one embodiment, liquid compositions as described herein can be administered from absorbent materials, such as a bandage, tampon or sponge, or as a spray/aerosol (applied to the affected area using a pump-type or aerosol sprayer). The use of a contraceptive sponge, in which the composition of the invention has been incorporated, is advantageous in that it the composition will be slowly and continuously released even though it may be continuously carried away by host activity or other vaginal discharge. Providing the composition in the form of a solution, which may initially be provided in a concentrated liquid form, or as a dissolvable powder, tablet or the like requiring the addition of water, saline or other suitable diluents prior to use, enables the composition to be administered as a vaginal douche.

In one embodiment, solid compositions can be applied by any number of means, including the use of applicators or by the subject's self-insertion. In another embodiment, creams, lotions, suppositories, foams, pastes, ointments, gels, or tablets may be administered using an applicator, such as a squeeze-type or plunger-type applicator. Administering the composition as a vaginal suppository is advantageous as it provides convenience, ease of application, increased safety and/or neatness. Administering the composition as a cream having low surface tension is advantageous as it provides a uniform coverage action that assists in composition penetration into crypts and crevices of the orifice. Such a creamy composition can in another embodiment also act as a moisturizer.

In one embodiment an aqueous gel containing a mucoadhesive material, such as carboxymethylcellulose (optionally mixed with a thermogelling mucoadhesive agent), is mixed with an agent capable of attaching to gp-340, an effective amount of an antibody or a fragment thereof specific against gp-340 that is expressed on the host cell surface, or a combination thereof to thereby form a composition of the invention. An additional embodiment provides for the encapsulation of an agent capable of attaching to gp-340, an effective amount of an antibody or a fragment thereof specific against gp-340 that is expressed on the host cell surface, or a combination thereof in polymeric microparticles. Once in situ, the polymer dissolves and the an agent capable of attaching to gp-340, an effective amount of an antibody or a fragment thereof specific against gp-340 that is expressed on the host cell surface, or a combination thereof is released. In one embodiment, release of an agent capable of attaching to gp-340, an effective amount of an antibody or a fragment thereof specific against gp-340 that is expressed on the host cell surface, or a combination thereof can be controlled by the microparticles to provide extended production of the desired product (e.g., sustained release). Appropriate modification of the delivery vehicles described herein is well within the skill of those in the art.

In one embodiment, the compositions described hereinabove are used in the methods described herein. In one embodiment, provided herein is a method of identifying therapeutic agents for inhibiting infection by an immunodeficiency virus of a host cell comprising the step of: injecting a gp-340 molecule to a mammal; and isolating antibodies or fragments specific to said gp-340 molecule, wherein said gp-340-specific antibodies or fragments thereof are capable of inhibiting the infusion and subsequent infection by immunodeficiency virus of a host cell. In another embodiment, the host cell for which identifying therapeutic agents for inhibiting infection by an immunodeficiency virus is sought, is a vaginal epithelial cell, or an endocervical or an ectocervical primary epithelial cell or their combination in other embodiments.

In one embodiment, provided herein is a method of preventing or inhibiting or suppressing attachment of an immunodeficiency virus to a host cell, such as genital epithelial cell in another embodiment, comprising the step of contacting the host cell with a gp340-specific antibody or a fragment thereof, thereby eliminating the attachment site on the host cell for the virus.

In one embodiment, any of the antibodies described hereinabove may be used in the method for preventing attachment of an immunodeficiency virus to a host cell, comprising the step of contacting the host cell with a gp340-specific antibody or a fragment thereof, thereby eliminating the attachment site on the host cell for the virus. In one embodiment, the host cell is a genital tract epithelial cell, or a vaginal, an endocervical or an ectocervical primary epithelial cell in other embodiments. In one embodiment, the antibody or fragment thereof is mAb116, mAb303, pAb1527, DAPA or their combination as described herein.

In one embodiment, provided herein is a method of inhibiting attachment of an immunodeficiency virus to a host cell, comprising the step of contacting gp-340 with an agent capable of attaching and blocking binding to the third hypervariable region of gp-120 (V3 loop) expressed on the virus' envelope.

In one embodiment, "contacting" a cell with a substance refers to (a) providing the substance to the environment of the cell (e.g., solution, in vitro culture medium, anatomic fluid or tissue) or (b) applying or providing the substance directly to the surface of the cell, in either case so that the substance comes in contact with the surface of the cell in a manner allowing for biological interactions between the cell and the substance.

In one embodiment, any of the compositions described hereinabove may be used for contacting the host cell, or the virus in the method for preventing attachment of an immunodeficiency virus to a host cell, comprising the step of contacting the host cell with a gp340-specific antibody or a fragment thereof, or an agent capable of attaching to the third hypervariable region of gp-120 (V3 loop) expressed on the virus' envelope, thereby eliminating the attachment site on the virus' envelope for gp-340, or their combination.

In one embodiment, the compositions described hereinabove, are used in the contraceptive devices described herein. In another embodiment, provided herein is a contraceptive device comprising: an effective amount of an agent capable of attaching to gp-340 and blocking binding of the third hypervariable region of gp-120 (V3 loop) expressed on an immunodeficiency virus' envelope; an effective amount of an antibody or a fragment thereof specific against gp-340 that is expressed on the surface of a vaginal, an endocervical or an ectocervical primary epithelial cell, or a combination thereof.

The contraceptives described herein include in one embodiment, spermicidal creams and gels. These products can be used alone or in conjunction with removable contraceptive devices, such as intrauterine devices. In one embodiment coating conventional contraceptive means with the compositions as described herein is done by priming conventional contraceptive means using a priming treatment, such as flame, or oxidizing acid, corona discharge or plasma; followed by coating the primed contraceptive means with a liquid solution of hydrogel polymer and absorbing the compositions described herein into the hydrogel polymer. The coating of conventional contraceptive means with the compositions described herein will result in one embodiment in enhanced conventional contraceptive means with decreased HIV infectivity. When in one embodiment, HIV is put into contact with such coated contraceptive means, the binding between immunodeficiency virus and gp-340, is inhibited through occupying the binding site for the virus and preventing binding of the virus onto the genital tract epithelial cell and subsequent infection of target cells. In another embodiment, the coated conventional contraceptive means have anti-bacterial and anti-viral activity.

In one embodiment, an delivery system suitable for use in accordance with the embodiments described herein comprises fibers or filaments comprising the active agents and biodegradable or nonbiodegradable polymers. Precision delivery systems can be mass-produced by this method; moreover, geometrically configured controlled-release devices can be produced in one embodiment by wrapping drug-releasing fibers around conventional intravaginal rings or other intravaginal devices. In another embodiment, fibrous delivery systems rely on membrane-moderated diffusion mechanisms to control the rate and duration of drug release. Monolithic drug-releasing fibers may be prepared by conventional spinning processes; when reservoir-type fibrous systems are desired, either a fast-releasing monolithic fiber is prepared and then coated with a rate-controlling sheath, or a coaxial spinning process is employed, in which the drug is extruded as the core of the fiber at the same time as the rate-controlling polymer sheath. Suitable fibers for providing zero-order release of the active agents and methods for the preparation thereof are described in Cowsar, D. E. and Dunn, R. L., "Biodegradable and Nonbiodegradable Fibrous Delivery Systems," in Zatuchni, G. L. et al. (eds.), Long-acting contraceptive delivery systems, pp. 145-163 (1984), the entire disclosure of which is hereby incorporated by reference.

Other suitable materials for preparation of such intravaginal devices include silicon-based materials, such as polydimethylsiloxanes in one embodiment, which have been employed to prepare capsule-type, matrix-type and microsealed drug delivery systems. In one embodiment, a device is prepared by coating a nonmedicated silicone rubber core with a thin layer of silicone rubber (such as MDX-4-4210 Clean Grade Elastomer, available from Dow Corning) which contains micronized crystalline forms of the active agents. An implant of this type (for administration of estradiol-17B) is described in Ferguson, T. H. et al., "Compudose: An Implant System for Growth Promotion and Feed Efficiency in Cattle," J. Controlled Release 8, pp. 45-54 (1988), the entire disclosure of which is hereby incorporated by reference. Improved devices may be prepared by incorporating water-soluble carriers, such as sodium alginate, or by using additives, such as co-solvents or salts, which enhance the release rate of active agents from the polymer matrix.

In one embodiment, contraceptive vaginal rings may be designed as homogeneous mixtures of the compositions described herein and silastic; as a core vaginal ring surrounded by silastic; as a shell ring with a core of silastic, surrounded by a layer of the compositions described herein and silastic covered by a tube of silastic; as a band ring of inert silastic with a drug-containing band on the ring; or as a combination of the various designs to permit the specific release characteristics desired. In this regard, useful systems are described in the following: Jackanicz, T. M., "Vaginal Ring Steroid-Releasing Systems," pp. 201-212; Diczfalusy, E. and Landgren, B.-M., "Some Pharmacokinetic and Pharmacodynamic Properties of Vaginal Delivery Systems That Release Small Amounts of Progestogens at a Near Zero-Order Rate," pp. 213-227; and Roy, S, and Mishell, Jr., D. R., "Vaginal Ring Clinical Studies: Update," pp. 581-594, all in Zatuchni, G. L. et al. (eds.), Long-acting contraceptive delivery systems (1984), the entire disclosures of which are hereby incorporated by reference.

In one embodiment, the contraceptive device comprising: an effective amount of an agent capable of attaching to gp-340 and blocking the binding of the third hypervariable region of gp-120 (V3 loop) expressed on an immunodeficiency virus' envelope; an effective amount of an antibody or a fragment thereof specific against gp-340 that is expressed on the surface of a vaginal, an endocervical or an ectocervical primary epithelial cell, or a combination thereof, is a condom, a sponge, a diaphragm, or an IUD or an IFD.

In another embodiment, any of the agents described in the methods for rational drug development described hereinbelow, may be used in the methods and compositions described herein. In another embodiment, provided herein is a method to identify a ligand to membrane bound gp340, comprising: contacting a membrane bound gp340 with a candidate ligand, under conditions wherein, in the absence of said candidate ligand, said membrane bound gp340 is capable of attaching to the third hypervariable region of gp-120 (V3 loop) expressed on an immunodifeciency virus' envelope; and detecting concentration or activity of bound virus' envelope, wherein reduction in concentration or activity of said bound virus' envelope in the manner associated with the binding of said membrane bound gp340 indicates that said candidate ligand is a membrane bound gp340 ligand.

In one embodiment, The term "ligand" or "candidate ligand" refers to a compound that possesses or has been modified to possess a reactive group that is capable of forming a covalent bond with a complimentary or compatible reactive group on a target. The reactive group on either the ligand candidate or the target can be masked with, for example, a protecting group. In one embodiment, the term "ligand" refers to an entity that possesses a measurable binding affinity for the target. In another embodiment, a ligand is said to have a measurable affinity if it binds to the target with a $K_d$ or a $K_i$ of less than about 100 mM. In certain embodiments, the ligand is not a peptide and is a small molecule. A ligand is a small molecule if it is less than about 2000 daltons in size, usually less than about 1500 daltons in size. In another embodiment, the small molecule ligand is less than about 1000 daltons in size, usually less than about 750 daltons in size, and more usually less than about 500 daltons in size.

Initially a potential ligand could be obtained by screening a random peptide library produced by recombinant bacteriophage in one embodiment, [Scott and Smith, Science, 249:386-390 (1990); Cwirla et al., Proc. Natl. Acad. Sci., 87:6378-6382 (1990); Devlin et al., Science, 249:404-406 (1990)] or a chemical library. An agent thus selected in another embodiment, could then be be systematically modified by computer modeling programs until one or more promising potential drugs are identified. Such analysis has been shown to be effective in the development of HIV protease inhibitors [Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1: 109-128 (1993)].

In one embodiment, computer modeling allows the selection of a finite number of rational chemical modifications, as opposed to the countless number of essentially random chemical modifications that could be made, any one of which might lead to a useful ligand. Each chemical modification requires additional chemical steps, which while being reasonable for the synthesis of a finite number of compounds, may become overwhelming if all possible modifications are needed to be synthesized. Thus through the use of a three-dimensional structural analysis and computer modeling, a large number of these compounds can be rapidly screened on the computer monitor screen, and a few likely candidates can be determined without the laborious synthesis of numerous compounds.

In one embodiment, provided herein is a method to identify a ligand to gp-340 that blocks the binding of the third hypervariable region of gp-120 (V3 loop) expressed on an immunodifeciency virus' envelope, comprising: and detecting concentration or activity of bound virus' envelope, wherein reduction in concentration or activity of said bound virus' envelope in the manner associated with the binding of said third hypervariable region of gp-120 (V3 loop) expressed on an immunodifeciency virus' envelope indicates that said candidate ligand is a third hypervariable region of gp-120 (V3 loop) ligand.

In one embodiment, both the ligand to the third hypervariable region of gp-120 (V3 loop) expressed on an immunodifeciency virus' envelope and the ligand to membrane bound gp340, which may be the same ligand in another embodiment, are the product of rational drug design.

In another embodiment, provided herein is a method of using a three-dimensional structure of membrane bound gp340 in an agent screening assay comprising the steps of: selecting a potential agent by performing rational drug design based on said three-dimensional structure, wherein said selecting is performed in conjunction with computer modeling; contacting the potential agent with a first polypeptide comprising an amino acid sequence having at least 75% homology to a first predetermined region of the membrane bound gp340; and detecting the binding affinity of the potential agent with said first polypeptide, whereby a potential agent is selected as an agent if the potential agent binds to said first polypeptide.

Once a potential agent or ligand is identified, in one embodiment it can either be selected from a library of chemicals that are commercially available from most large chemical companies including Merck, Glaxo Welcome, Bristol Meyers Squib, Monsanto/Searle, Eli Lilly, Novartis and Pharmacia UpJohn, or in another embodiment the potential drug may be synthesized de novo. As mentioned herein, the de novo synthesis of one or even a relatively small group of specific agents or ligands is reasonable experimentation for rational drug design.

The potential agent or ligand can be tested in one embodiment by any standard binding assay (including in high throughput binding assays) for its ability to inhibit the binding of HIV to genital tract epithelial cell as described herein. In another embodiment the potential agent or ligand can be tested for its ability to bind to membrane bound gp340. When a suitable potential ligand or agent is identified, a second NMR, or other proper spectroscopic methods of structural analysis can optionally be performed on the binding complex formed between the potential agent or ligand and their target molecule. Computer programs that can be used to aid in solving the three-dimensional structure of menins and binding complexes thereof include QUANTA, CHARMM, INSIGHT, SYBYL, MACROMODE, and ICM, MOLMOL, RASMOL, AND GRASP [Kraulis, J. Appl Crystallogr. 24:946-950 (1991)]. Most if not all of these programs and others as well can be also obtained from the WorldWideWeb through the internet.

RDD has been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods may be used in certain embodiments to selectively isolate and subsequently analyze binding components of mixtures of compounds.

In another embodiment, ACE-ESI-MS, uses affinity capillary electrophoresis to accomplish the separation of noncovalent complexes formed upon mixing a biomolecular target such as menin in one embodiment, with a combinatorial library or mixture of compounds. The biomolecular target is typically incorporated into the capillary so that those ligands present in the combinatorial mixture interact with the target and are retained or slowed down within the capillary. Once separated, these noncovalent complexes are analyzed on-line by ESI-MS to ascertain the structures of the complexes and bound components. In another embodiment, size-exclusion chromatography (SEC) followed by LC/MS or CE/MS analysis is used in the determination of affinity or biological function in the methods described herein. Size exclusion is a method to separate a biopolymer target and its complexes with small molecules members of a combinatorial library. Once isolated by SEC, these complexes are dissociated, under denaturing solution conditions, and finally the binding ligands are analyzed by mass spectrometry.

In one embodiment, Bio-affinity characterization mass spectrometry (BACMS) is used for the characterization of noncovalent interactions of mixtures of ligands and biomolecular targets according to the methods described herein. BACMS involves in one embodiment, the electrospray ionization of a solution containing both the affinity target and a mixture of ligands (or a combinatorial library), followed by trapping of all the ionic species in the FTICR ion-trap. The complexes of interest are then identified in the mass spectrum and isolated by selected-ion accumulation. This is followed by low energy dissociation. or 'heating' to separate the higher binding affinity ligands present in the complex. Finally, collisionally activated dissociation (CAD) is used to provide structural information about the high binding affinity ligand. In one embodiment, using BACMS allows for the time-consuming techniques usually needed for the study of libraries, such as affinity chromatography, using solid supports for separation and purification of the complexes, followed by analysis to characterize the selected ligands, are all combined into one FTICR-MS experiment. In one embodiment BACMS is applied as a research tool to the study of HIV binding to genital tract epithelial cells.

In one embodiment, provided herein is a method of using a three-dimensional structure of membrane bound gp340 in an agent screening assay comprising the steps of: selecting a potential agent by performing rational drug design based on said three-dimensional structure, wherein said selecting is performed in conjunction with computer modeling; contacting the potential agent with a first polypeptide comprising an amino acid sequence having at least 75% homology to a first predetermined region of the membrane bound gp340; and detecting the binding affinity of the potential agent with said first polypeptide; contacting the bound potential agent with a second polypeptide comprising an amino acid sequence having at least 75% homology to a second predetermined region of the third hypervariable region of gp-120 (V3 loop) expressed on an immunodifeciency virus' envelope; and detecting the binding affinity of the potential agent with said second polypeptide, whereby a potential agent is selected as an agent if the potential agent binds to said first and second polypeptide.

In another embodiment, the first predetermined regions used in the method of using a three-dimensional structure of membrane bound gp340 in an agent screening assay are selected based on the three-dimensional structure of membrane bound gp340 and are binding regions in one embodiment, or a catalitic region, structural region or the whole membrane bound gp340 in other embodiments. In one embodiment, the predetermined region is selected from the three-dimensional structure of a protein having structural similarity to the membrane bound gp340.

In one embodiment, the second predetermined regions used, in the method of using a three-dimensional structure of membrane bound gp340 in an agent screening assay are selected based on the three-dimensional structure of the third hypervariable region of gp-120 (V3 loop) expressed on an immunodifeciency virus' envelope and are binding regions in one embodiment, or a catalitic region, structural region or the whole V3 loop expressed on the immunodificiency virus.

In one embodiment, the ligand or agents identified by the methods described hereinabove are used in a composition for inhibiting trans-infection by an immunodeficiency virus of a genital tract epithelial cell in a subject.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Materials and Methods
Virus, Cell lines, Antibodies and Inhibitors.

HIV-1 BL-2, Ba-L, 89.6 and MB viruses were obtained from the Center for AIDS Research (CFAR) at the University of Pennsylvania, Philadelphia, Pa. 293 and FaDu cells (ATCC) were grown in DMEM supplemented with 10% FBS and 2 mM L-glutamine (Invitrogen). AGS cells (ATCC) were grown in F12 supplemented with 10% FBS and 2 mM L-glutamine. VK2E6E7, Endo1E6E7 and Ect1E6E7 cell lines were obtained from R. Fichorova (Fearing Research Laboratory, Boston, Mass.) and grown in KFM media (Invitrogen) as described (Fichorova, R. N., J. G. Rheinwald, and D. J. Anderson. 1997. Generation of papillomavirus-immortalized cell lines from normal human ectocervical, endocervical, and vaginal epithelium that maintain expression of tissue-specific differentiation proteins. *Biol Reprod* 57, 847-855). Gp-340-specific monoclonal antibodies 303 mAb and 116, mouse polyclonal antibody DAPA, and rabbit polyclonal antibody 1527 were used. HIV-1 V3 loop-specific peptides 6283, VQINCTRPNYNKRKR (SEQ ID NO. 1), and 6284, CTRPNYNKRRIHIG (SEQ ID NO. 2), and control peptide 6220, KEATTTLFCASDAKA (SEQ ID NO. 3), scrambled 6284, RCIHNRTIKGPYNKR (SEQ ID NO. 4), were obtained from the AIDS Reference and Reagent Program. pDEST-DMBT1 was obtained from U. Holmskov (University of Southern Denmark, Odense, Denmark).

Stable Clone Construction and Selection 293 cells were transfected with pDEST-DMBT1 in Fugene 6 (Roche Diagnostics) per manufacturer's instructions and selected with 500 µg/mL G418 (Invitrogen). Potential clones were measured for extra- and intracellular expression of gp-340 by flow cytometry as described below.

Cellular Staining for Expression of gp-340

Cells were grown in 6-well plates and removed with PBS w/o $Ca^{++}$ or $Mg^{++}$ with 5 mM EDTA. Optimal staining was observed when 4 mM $Ca^{++}$ was used throughout the staining. Polyclonal antibody 1527 in PBS 2% FCS 4 mM $Ca^{++}$ was added to disrupted cells for 20 minutes on ice. For intracellular to protein analysis, saponin (Sigma) (0.25%) was added to all staining steps. PE-conjugated Goat F(ab)' anti-rabbit IgG (CalTag) was used as a secondary antibody. Cells were analyzed on a FACScan flow cytometer (Becton-Dickinson) using Cell Quest Pro software.

PBMC Purification and Stimulation.

PBMCs of healthy volunteers were isolated from leukapheresis packs obtained under an institutional review board-approved protocol. Cells were subjected to Ficoll-Hypaque density gradient centrifugation. Purified PBMCs were stimulated in RPMI 1640 supplemented with 10% FBS and 2 mM L-glutamine (complete medium) plus 4 µg/ml PHA (Sigma-Aldrich) and 20 U/ml IL-2 (AIDS Reference and Reagent Program) at 37° C. for 48 hours, washed and cultured in IL-2 (20 U/ml).

Trans-Infection Assay.

Parental or gp-340 expressing 293 cells, VK2E6E7, Endo1E6E7, Ect1E6E7, or AGS cells or 1 mm³ pieces of ectocervix obtained as described below seeded in 96 well plates were incubated with various IU inputs of HIV, in 100 µl final volume for 2 h at 37° C. and then extensively washed. Additional inhibitors, peptides or antibodies, were added to cells 30 min prior to pulsing with virus and replaced after cells were washed. Plates were centrifuged at 1250 rpm for 7 minutes between each wash. After viral incubation and washing, PHA-blasts were cocultured with the pulsed cells for 7 days at 37° C. with IL-2. Infection was monitored by measuring supernatant-associated p24 Gag protein content on day 7. $TCID_{50}$ was calculated using the Reed-Münch formula.

Tissue Isolation, Staining and Analysis

Fresh vaginal and cervical tissues were obtained during total abdominal' hysterectomy from the Cooperative Human Tissue Network (University of Pennsylvania). Tissue was frozen, sectioned and stained with 303 mAb and goat anti-mouse Ig-peroxidase and then counterstained with hematoxylin.

Transcytosis Assay

HEC1A is a cell line capable of forming tight junctions and it is applied to the top chamber of a transwell and allowed to grow until resistance indicating no open connections between chambers is obtained. HIV is applied to the top chamber and the bottom chamber is sampled at various time points. The amount of HIV that is transcytosed is determined by p24 Gag ELISA or gag real time PCR.

Example 1

Cell Surface Expression of gp-340 Enhances HIV Trans-Infection

Secreted gp-340 found at high levels in the oral cavity and also exists in a cell surface-associated form, although mRNA containing exon 55, which encodes the putative transmembrane domain, has not yet been detected. Cell lines expressing gp-340 on their extracellular membranes were established by transfecting plasmids encoding the full length gp-340 (exon 1-54) (FIG. 1a). Of interest, control untransfected 293 cells had very low levels of endogenous gp-340 as did many human-derived epithelial and myeloid cell lines (FIG. 1a). The gp-340 expressing cell lines were measured for their ability to transmit cell-free HIV to human PHA- and IL-2-stimulated PBMCs (PHA-blasts). Transfected cells were incubated with or without HIV-1-specific peptide 6284, derived from the base of the V3 loop that has been shown to block Env binding to gp-340. Decreasing amounts of HIV (primary M-tropic strain BL2) were added and incubated with the cells in the continued presence of peptide 6284. After extensive washing, the cells were cocultured for 7 days with PHA-blasts. Infection was monitored by p24 Gag protein content in the culture supernatant in each well and scored for the presence or absence of infection. The assay used 6 replicates of cells for each viral dilution and condition and calculated the number of wells that became infected at each amount of added virus. Thus, a finding that 50% of the wells became infected when 0.11 IU were added and 100% of the wells became infected when 0.33 IU of HIV were added for gp-340 expressing 293 cells determines that gp-340 increased the $TCID_{50}$ of the added virus approximately 6 fold compared to that of the non-exogenously expressing 293 cells (FIG. 1b). When gp-340-expressing cells were pre-incubated with peptide 6284 corresponding to HIV-1 Env, the enhancement was abolished (FIG. 1b). To demonstrate statistical significance, comparisons of the average p24 in the 6 wells for each condition at each viral input were performed. The difference between transmission by clone 1D4 in the presence or absence of peptide 6284 (mean P24 of 7 vs 239 at 0.33 and 7 vs 184 at 0.11) was significant at 0.33 and 0.11 IUs (p=0.03, for both) The addition of peptide 6284 to PHA-blasts prior to HIV did not affect their infection. Other transfected 293 clones expressing gp-340 could transmit HIV to target cells to a degree that correlated strongly with their overall expression levels. None of the transfected 293 clones or untransfected 293 cells could replicate virus in the absence of coculture. 293 cells transfected with gp-340 also released soluble gp-340 into the supernatant. Since soluble gp-340 has previously been demonstrated to inhibit HIV infection, it is possible that the enhancement of HIV infectivity by cell surface gp-340 is more than six-fold. Trypsin treatment of HIV pulsed cells demonstrated that a portion of the pulsed virus was in a trypsin sensitive compartment, likely the cell surface, while the majority of the virus was resistant to trypsin, potentially intracellular (FIG. 1c).

Example 2

Figure 2:
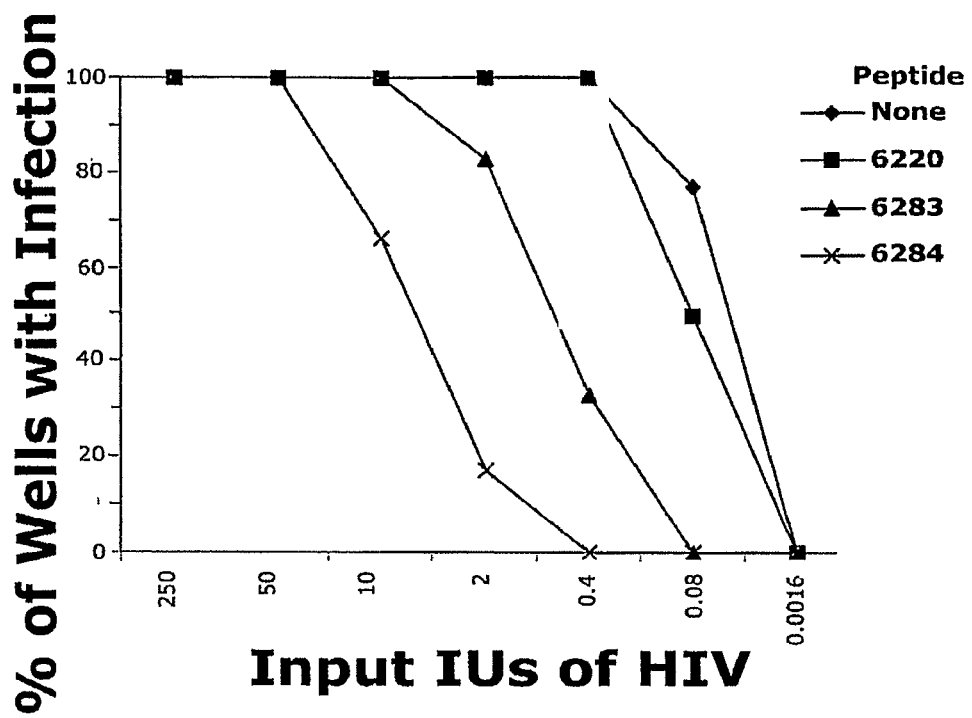
FIG. 2 Transmission of HIV by AGS cells expressing endogenous gp-340 is inhibited by peptide corresponding to the V3 domain of Env. AGS cells were preincubated with gp-340-specific peptide 6283 or 6284, and control peptide 6220 (10 μg/ml) for 15 min and then pulsed with decreasing amounts of HIV strain BL2. After viral exposure, the cells were washed four times to remove unbound virus and cocultured with T cell blasts in the absence of peptides for 24 h. The T cell blasts were then moved to new wells and p24 Gag antigen content was measured 7 days later. IUs were calculated using PHA-blasts as target cells in a $TCID_{50}$ assay. Experiment was performed in replicates of six per virus concentration. Data is expressed as the percentage of the 6 wells in which the cells became infected for each virus concentration.

AGS Cells that Express GP-340 can Bind HIV and Transmit the Virus to Target Cells To examine native expressed gp-340, the gastrointestinal carcinoma cell line AGS, which is expresses gp-340, was analyzed for its ability to transmit HIV in vitro. AGS cells enhanced transmission of HIV to target $CD4^+$ T cells. Cells were infected in 50% of the wells when 0.08 infectious units (IU) of virus were pulsed per well. This represented a 6-fold enhancement in the viral infectivity by gp-340. Peptides 6283 and 6284, derived from the proposed gp-340 binding site in Env, abolished the enhancement in infectivity. Control peptide 6220, derived from another part of Env, had no impact on the enhancement in infectivity (FIG. 2). The difference between peptide 6284 and control peptide 6220 was significant at viral inputs of 2, 0.4 and 0.08 IUs (p=0.03, 0.01 and 0.02, respectively). For peptide 6283 compared to peptide 6220, statistical significance was found at viral inputs of 0.4 and 0.08 Rh (p=0.05 and 0.04, respectively for peptide 6220) The magnitude of the inhibition by the active peptides correlated closely with the affinity with which these peptides interacted with gp-340.

Example 3

Vaginal and Cervical Epithelia Express gp-340

Figure 3:
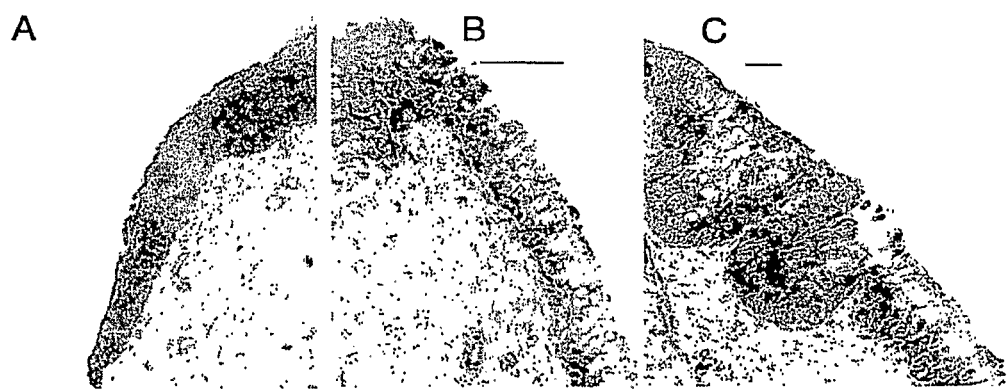
FIG. 3 shows human genital tract tissues express gp-340. Physiologically normal vaginal (A) and cervical (B and C) tissues were stained with mouse anti-gp-340 mAb 303. Cell nuclei were counterstained with hematoxylin. Bars represent 25 μm.

Physiologically normal genital tract tissue was obtained from subjects undergoing total abdominal hysterectomy. Tissue sections were immunohistochemically stained for gp-340 with a specific monoclonal antibody. In the vaginal epithelium, the stratified squamous epithelia showed significant and diffuse expression of gp-340 (FIG. 3a). Expression in cervical tissue was seen both on the outer luminal surface of the columnar epithelial cells, but most strongly along the basilar region (FIGS. 3b and c). Expression patterns between 3 independent donors were comparable.

Example 4

Figure 4:
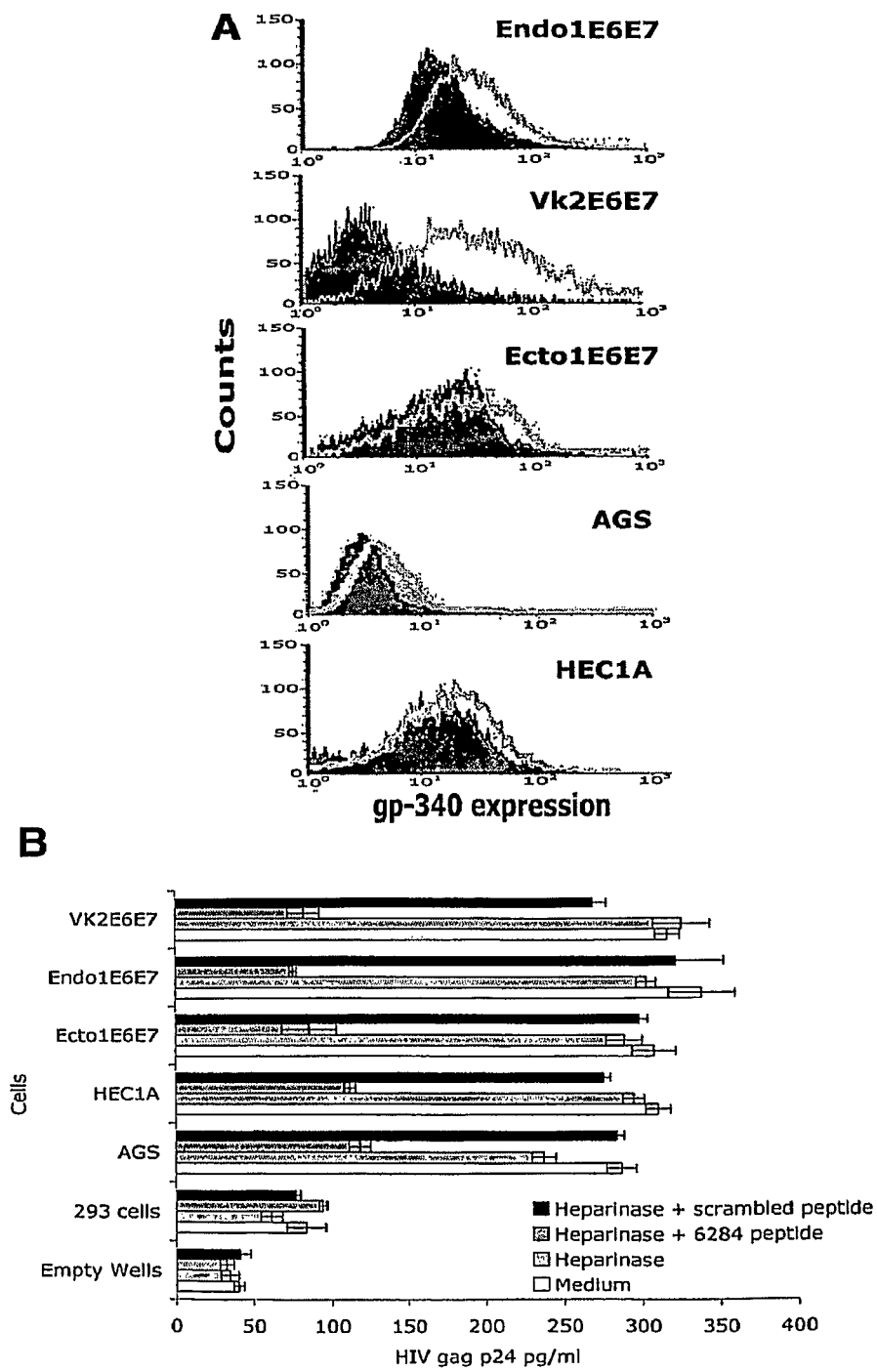
FIG. 4 shows cell lines derived from human cervical, vaginal, and intestinal epithelium express gp-340. (A) Endo1E6E7, VK2E6E7, Ect1E6E7, HEC1A and AGS cells were stained with gp-340-specific mAb 116 followed by goat anti-mouse IgG-PE secondary antibody. Cells were analyzed on a FACScan flow cytometer. ■ represent isotype control staining and ■ present mAb 116 staining. (B) 293, VK2E6E7, Endo1E6E7, Ecto1E6E7, AGS and HEC1A cells were pretreated with medium alone, to peptide 6284 (10 μg/ml) and Heparinase III (5 U/ml), scrambled peptide 6284 (10 μg/ml) and Heparinase III, or Heparinase III alone. Cells were then pulsed with BL2 virus (5 ng/well). Following washing, the cells were lysed and measured for p24 content by ELISA. Experiments were performed in four well replicates. Error bars reflect standard deviation.

Primary Vaginal and Cervical Cell Lines Express gp-340 and Transmit HIV to PHA-Blasts Human papiloma virus E6 and E7 gene transformed vaginal, endocervical and ectocervical primary epithelial cells (VK2E6E7, Endo1E6E7 and Ect1E6E7, respectively) were obtained from Dr. Raina Fichorova (Boston, Mass.). All of these cell lines expressed detectable levels of gp-340 on the cell surface by FACS analysis (FIG. 4). Each cell line was tested for their ability to transmit cell-free virus to target PHA-blasts. FaDu, a pharyngeal epithelial cell line that does not express gp-340, was used as control. To determine the contribution of gp-340 in the context of other HIV binding macromolecules that could be present on these cells, gp-340-specific antibodies and HIV-specific peptides that block the interaction of gp-340 with Env were used.

Figure 5:
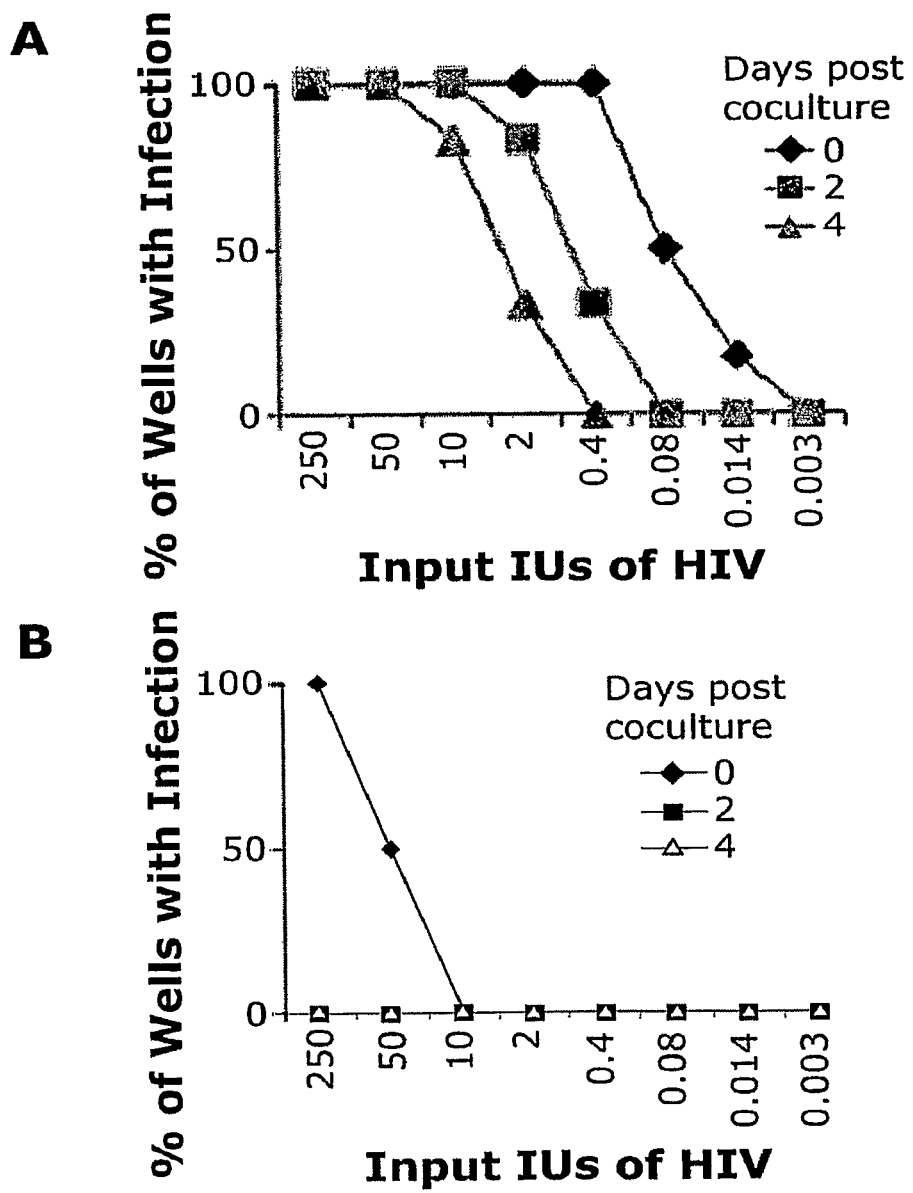
FIG. 5 shows genital tract epithelial cell lines trans-infect (transfer infectious virus to target cells) HIV-1. Ectocervical epithelial cells (Ect1E6E7) (A) and a pharyngeal epithelial cell line control FaDu (B) were pulsed with decreasing IU of HIV Ba-L and then washed 4 times. Either immediately or 2 or 4 days later, PHA-blasts were added. PHA-blasts were removed from Ect1E6E7 and FaDu cells after 18 h and cultured. Seven days post coculture, supernatant-associated p24 Gag protein content was measured by ELISA. IUs were calculated using PHA-blasts as target cells in a $TCID_{50}$ assay. Data is expressed as the percentage of wells containing cells demonstrating infection for each amount of virus added.
Figure 6:
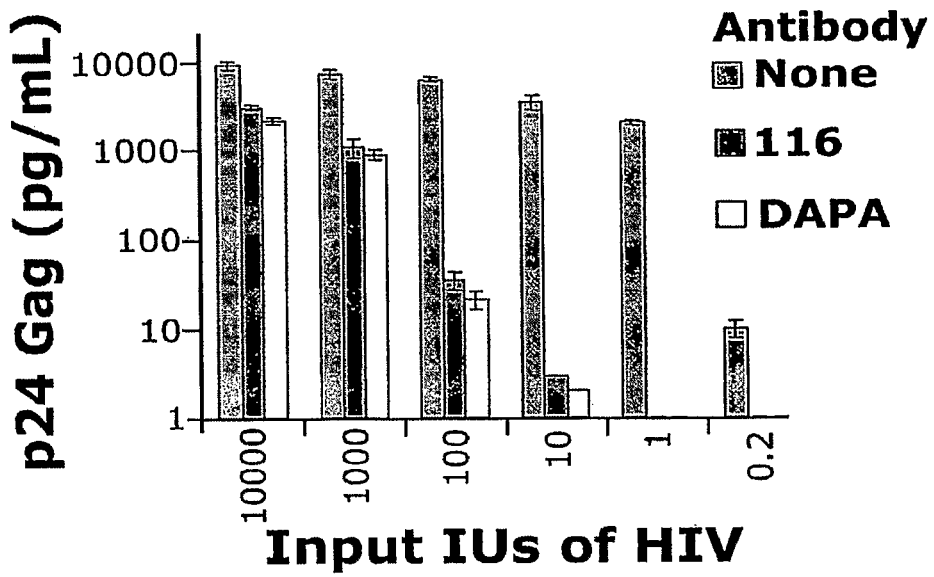
FIG. 6 shows transmission of HIV-1 by vaginal epithelial cells to target T cells in culture is mediated by gp-340. Vaginal epithelial cells (VK2E6E7) were incubated with isotype control or gp-340-specific antibodies 116 or DAPA and then pulsed with HIV-1 BL2 virus. After extensive washing, PHA-blasts were added for 24 h and then moved to new plates without VK2E6E7 cells. After 7 days, p24 Gag protein content in the supernatant was measured. Samples were run in triplicate and standard error of the mean is given.

Cell lines were pulsed with decreasing amounts of HIV Ba-L, washed and had target cells immediately added or added after 2 or 4 days of culture. When FaDu cells were pulsed with 250 Ms of HIV, less than 10% of the added virus could be recovered following immediate coculture and infectivity was lost when virus was incubated with the cells for 2 or 4 days prior to coculture (FIG. 5a). Adding 0.08 Ws of HIV to Ect1E6E7 cells led to infection in every well and virus incubated with Ect1E6E7 for 4 days remained infectious (FIG. 5b). Similar results were obtained using the VK2E6E7 and Endo1E6E7 cell lines, or when BL2, 89.6 and IIIB viral strains of HIV-1 were used. Trypsinization with a protocol that completely removed surface bound virus 2 hr after viral pulsing reduced (approximately 40%) but did not abolish infection in cocultured target cells. None of the genital tract-related cell lines replicated virus in the absence of coculture with target cells (FIG. 5c). To confirm the contribution of gp-340 to the observed increase in viral transmission associated with the genital tract epithelial cell lines, cells were incubated with gp-340 specific antibodies (116 and DAPA). The ability of VK2E6E7 cells to bind and transmit HIV to PHA-blasts was markedly decreased by pre-incubation with these gp-340-specific antibodies that were previously demonstrated to inhibit Env binding to gp-340 (FIG. 6). Similar levels of decrease in transmission were observed when peptide 6284 was added at the time of viral pulsing of VK2E6E7 cells. The observation that both multiple gp-340 specific antibodies that inhibit Env binding and HIV V3 derived peptides that inhibit gp-340-Env interaction reduced genital tract cell line mediated trans-infection demonstrates that gp-340 mediated this effect. A specific arginine in the V3 region mediates binding to syndecan and while our inhibitory peptides contain this amino acid, we demonstrate that syndecans do not mediate the transinfection. First, no effect on trans-infection by heparinase treatment that completely removes syndecan expression, as documented by flow cytometry, was observed. In addition, although the endocervical cell line EndoE6E7 showed low, but detectable levels of syndecans, the vaginal and ectocervical cell lines did not show surface syndecan expression by flow cytometry. These cell lines showed comparable abilities to trans-infect after heparinase treatment.

The above results show that inhibiting the interaction between gp340 and HIV Env proteins is efficacious for impeding HIV-1 infection.

Example 5

Figure 7:
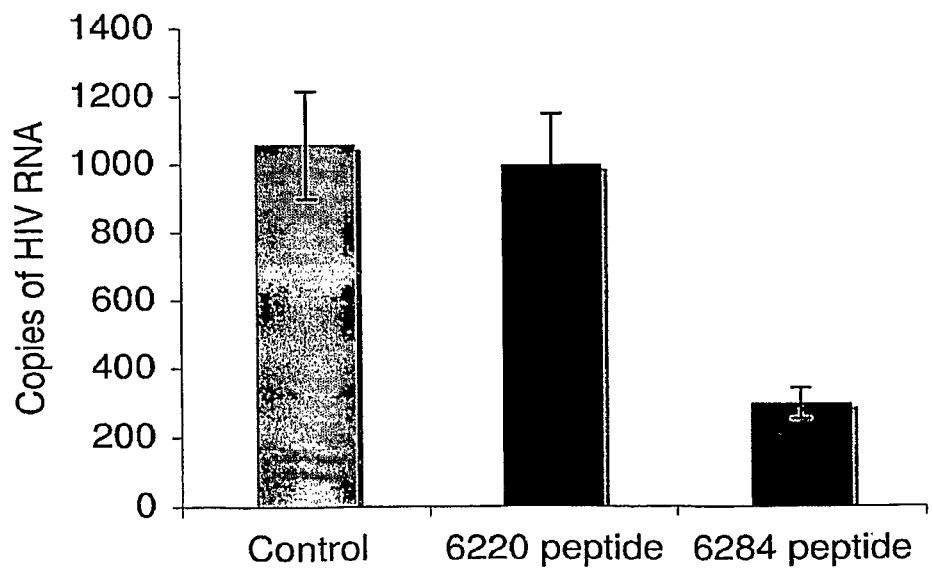
FIG. 7 shows that HEC1A cells transcytose HIV, which is blocked by HIV V3 loop peptide. HEC1A cells were grown on a transwell insert until a tight junction layer developed. This was documented by measuring the resistance across the cells. Then HIV-1 Ba-L was applied to the top well (1 ng) with 10 ug/ml peptide and supernatant collected from the bottom well 2 h later. The number of copies of HIV RNA was measured by real time PCR using HIV gag primers and probe. A standard curve was constructed with ACH2 cells.
Figure 8:
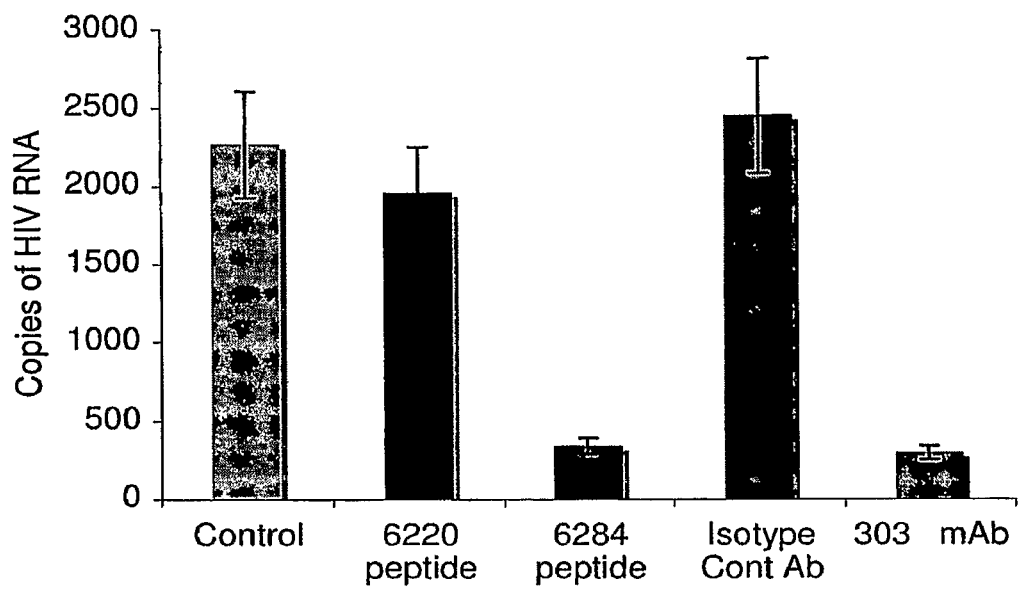
FIG. 8 shows that HEC1A cells transcytose HIV, which is blocked by HIV V3 loop peptide and GP340 specific Ab. The experiment was performed as described for FIG. 7 with the addition of peptide to (10 ug/ml) or antibody (10 ug/ml) to the top well. Copies of HIV in the bottom well were calculated as above.

Inhibiting HIV V3 Loop Peptide Inhibits HIV Transfection in Genital Tract Tissue As shown in FIG. 7, HEC1A cells were grown on the insert described above in the transcytosis section of the methodology, until a solid monolayer occurred. This was documented by measuring the resistance of the monolayer. HIV was added to the top and the amount that moved through the cells was measured in the bottom and is expressed on this graph. This shows that HIV can pass through cells and this can be inhibited with the described GP340 inhibiting peptide, showing (FIG. 8) that a GP340 specific antibody can inhibit transcytosis.

Figure 9:
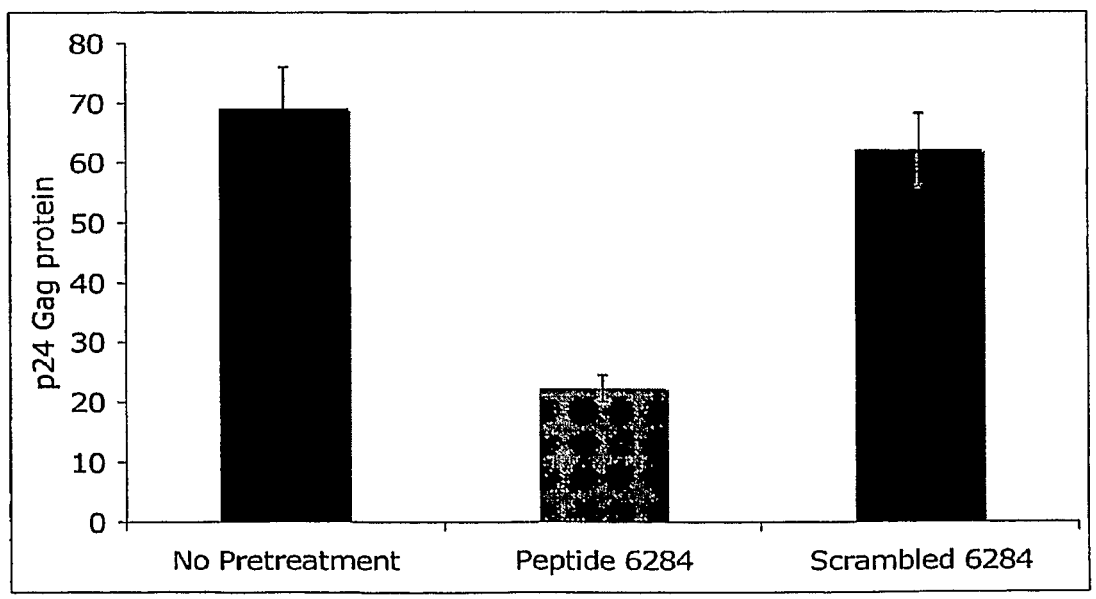
FIG. 9 shows viral binding by genital tract tissue. Ectocervical tissue was obtained post TAH-BSO and cut into 1 $mm^3$ pieces and placed into 48-well plates. HIV BL2 1 ng/well was added for 2 h at 37° C. and then the tissue was washed 6 times with PBS containing 4 mM $Ca^{++}$. The tissue was then lysed in cell culture lysis reagent (Promega) (200 ul/well) and p24 Gag protein was measured by ELISA.
Figure 10:
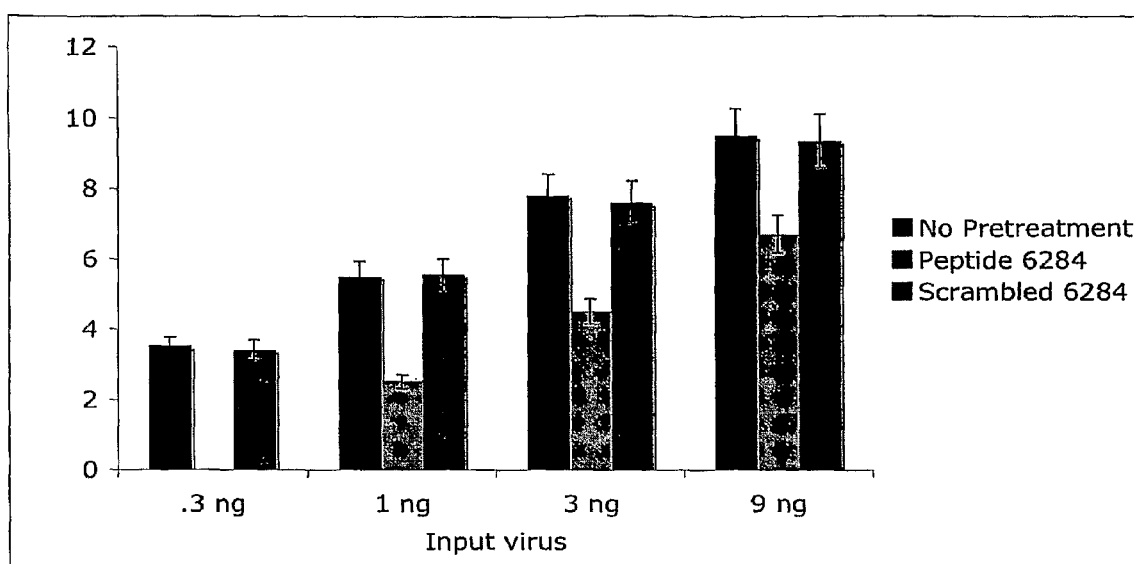
FIG. 10 shows Genital tract tissue transinfects HIV, which is blocked by HIV V3 loop peptide. Ectocervical tissue was prepared and HIV pulsed as described for FIG. 9. Instead of lysing the tissue, PHA-blasts were added and cultured for 7 days and then p24 Gag protein in the supernatant was measured by ELISA.

HIV bound to genital tract tissue can pass the virus to target cells (PHA-blasts) and cause infection of these cells (FIG. 10). As shown in FIG. 9, the ability of HIV to bind to genital tract tissue was measured showing that the binding of HIV can be inhibited by a peptide that blocks HIV binding to GP340.

All publications, patents, and patent applications cited herein are hereby incorporated by reference in their entirety for all purposes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of inhibiting binding of a human immunodeficiency virus (HIV) to a genital tract tissue in a subject, comprising the step of: contacting the genital tract with an effective amount of an agent capable of inhibiting the binding between immunodeficiency virus and gp-340, wherein said agent inhibits binding of gp-120 with gp-340 and is selected from the group consisting of a V3 loop-specific peptide and an antibody or functional fragment thereof, wherein the antibody is a monoclonal antibody (mAb), a polyclonal antibody (pAb), or a humanized antibody specific against gp-340, wherein the V3 loop-specific peptide comprises a contiguous gp-120 V3 loop sequence at least 15 amino acid long, and wherein the antibody against gp-340 is specific for a Lewis Y ($Le^Y$) epitope.

2. The method of claim 1, wherein the V3 loop-specific peptide comprises the amino acid sequence set forth in SEQ ID NO. 1, SEQ ID NO. 2 or a combination thereof.

3. The method of claim 1, wherein said fragment is Fc, Fab, F(ab')2, scFv or a combination thereof.

4. The method of claim 1, further comprising the step of administering to the subject an effective amount of a soluble gp-340, gp-340 mimetic or a combination thereof.

5. The method of claim 1, further comprising the step of administering to the subject an effective amount of 2,5-dimethoxy-substituted 5-bromopyridyl thiourea (PHI-236), nonoxynol-9 or a combination thereof.

6. A method of inhibiting attachment of a human immunodeficiency virus (HIV) to a host cell, comprising the step of contacting a gp340 protein expressed on the host cell with an agent capable of inhibiting attachment, wherein said agent inhibits binding of gp-120 with gp-340 and is a V3 loop-specific peptide or a gp340-specific antibody or a functional fragment thereof, wherein said antibody is a monoclonal antibody (mAb), a polyclonal antibody (pAb), or a humanized antibody, wherein the V3 loop-specific peptide comprises a contiguous gp-120 V3 loop sequence at least 15 amino acid long, and wherein the antibody against gp-340 is specific for a Lewis Y ($Le^Y$) epitope.

7. The method of claim 6, wherein said fragment is Fc, Fab, F(ab')2, scFv or a combination thereof.

8. The method of claim 6, wherein the host cell is a vaginal, an endocervical or an ectocervical primary epithelial cell.

9. The method of claim 6, wherein the V3 loop-specific peptide comprises the amino acid sequence set forth in SEQ ID NO. 1, SEQ ID NO. 2 or their combination.

10. The method of claim 6, further comprising contacting the virus with 2,5-dimethoxy-substituted 5-bromopyridyl thiourea (PHI-236), nonoxynol-9, or a combination thereof.

* * * * *

UNITED STATES PATENT AND TRADEMARK OFFICE
CERTIFICATE OF CORRECTION

PATENT NO. : 9,580,473 B2
APPLICATION NO. : 12/303985
DATED : February 28, 2017
INVENTOR(S) : Drew Weissman It is certified that error appears in the above-identified patent and that said Letters Patent is hereby corrected as shown below:

In the Specification

In Column 1, Line 5, please insert the following paragraph:
-- GOVERNMENT INTEREST STATEMENT
This invention was made with government support under grant numbers AI060505 and AI082701 awarded by the National Institutes of Health. The government has certain rights in the invention. --

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*